United States Patent [19]

Nishio et al.

[11] Patent Number: 4,883,643
[45] Date of Patent: Nov. 28, 1989

[54] OXYGEN SENSOR PROTECTED AGAINST CONTAMINANTS

[75] Inventors: Hisaharu Nishio; Toshio Okumura, both of Aichi, Japan

[73] Assignee: NGK Spark Plug Co., Ltd., Aichi, Japan

[21] Appl. No.: 332,425

[22] Filed: Mar. 28, 1989

Related U.S. Application Data

[63] Continuation of Ser. No. 129,878, Dec. 4, 1987, abandoned, which is a continuation of Ser. No. 876,061, Jun. 19, 1986, abandoned.

[30] Foreign Application Priority Data

Jun. 20, 1985 [JP] Japan .................................. 60-931169

[51] Int. Cl.[4] ............................................ G01N 31/12
[52] U.S. Cl. ........................................ 422/94; 422/95; 422/98; 436/127; 204/424; 204/428; 204/429; 338/34; 73/23; 73/27 R; 340/632
[58] Field of Search ............... 73/23, 27 R; 204/424, 204/425, 426, 427, 428, 429; 338/34; 340/632, 633, 634; 422/94, 95, 96, 97, 98; 436/127, 137

[56] References Cited

U.S. PATENT DOCUMENTS

| 4,187,163 | 2/1980 | Steinke et al. | 204/428 |
| 4,210,510 | 7/1980 | Grimes | 204/195 S |
| 4,323,440 | 4/1982 | Akatsuka | 204/428 |
| 4,362,609 | 12/1982 | Sano et al. | 204/428 |
| 4,417,888 | 11/1983 | Cosentino et al. | 604/29 X |
| 4,560,463 | 12/1985 | Frey et al. | 204/428 X |

FOREIGN PATENT DOCUMENTS 57-178152 11/1982 Japan .................................. 204/428

OTHER PUBLICATIONS

Hawley; Condensed Chemical Dictionary, 10th Edition, Van Nostrand Reinhold Co., New York, 1981, p. 832.

Primary Examiner—David L. Lacey
Assistant Examiner—L. Johnson
Attorney, Agent, or Firm—Sughrue, Mion, Zinn, Macpeak & Seas

[57] ABSTRACT

An electrolytic oxygen sensor in which the atmosphere is admitted to one side of the solid electrolyte through an air-permeable spacer through a dual concentric tube structure. Holes are formed in the inner tube to complete the air flow to the atmosphere. The small size of the holes prevent the entry of water and oil contaminants.

6 Claims, 5 Drawing Sheets

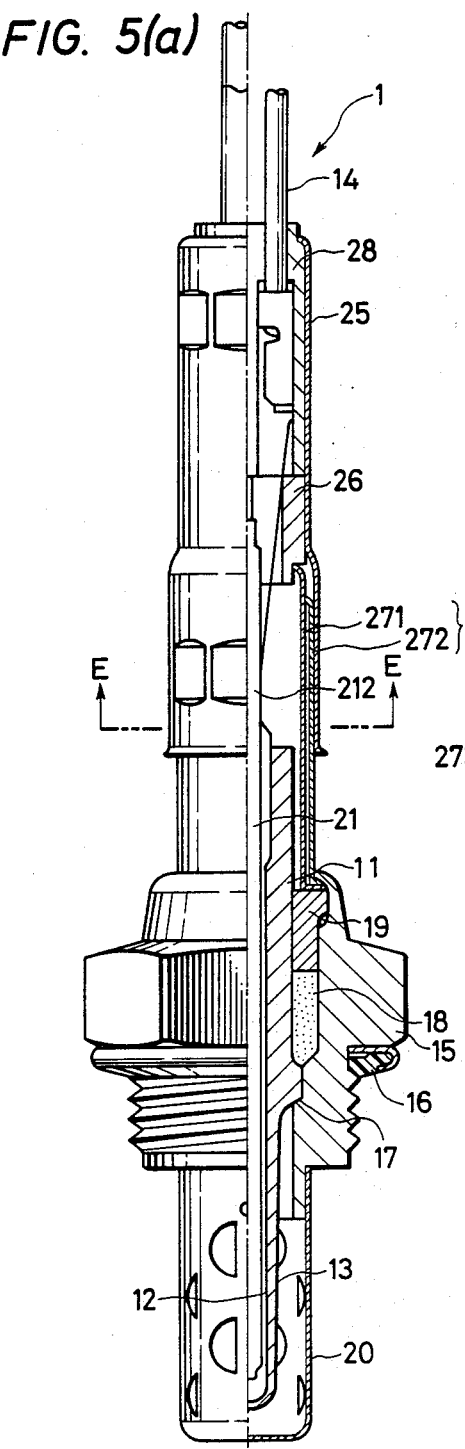
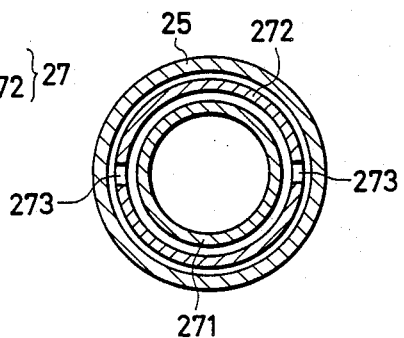
FIG. 5(a)
FIG. 5(b)

OXYGEN SENSOR PROTECTED AGAINST CONTAMINANTS

This application is a continuation of application Ser. No. 129,878 filed 12/4/87, now abandoned, which is a continuation of application Ser. No. 876,061 filed 6/19/86, now abandoned.

BACKGROUND OF THE INVENTION

1. Field of the Invention

The present invention relates to an oxygen sensor for detecting the concentration of oxygen in exhaust gas from internal combustion engines or other burning devices.

2. Background Art

Most of the oxygen sensors used heretofore in detecting the concentration of oxygen in exhaust gas from internal combustion engines or other burning devices employ oxygen detecting elements made of zirconia or other solid electrolytes.

In a typical case, an oxygen sensor of this sort comprises an oxygen detecting element in a tubular form of a solid electrolyte such as zirconia which is closed at one end and open at the other end. Inner and outer conductive layers usually made of platinum are deposited on the inner and outer sides, respectively, of said oxygen detecting element. An output terminal with air holes provides communication between the atmospheric air and the atmosphere within the oxygen detecting element. A lead wire picks up an electrical output from the inner conductive layer which is electrically connected to the lead wire through the output terminal. An outer tube accommodates the oxygen detecting element and the output terminal and is provided with air holes for providing communication between the atmospheric air and the atmosphere within the oxygen detecting element. In order to detect the concentration of oxygen in exhaust gas from a burner, the sensor is attached to the burner in such a manner that the inner conductive layer is in contact with the atmospheric air while the outer conductive layer is in contact with the exhaust gas.

When the oxygen sensor having the construction described above is used as an attachment to an internal combustion engine or a burning device, the inner conductive layer in the sensor may be contaminated with the oil or water present in the environment of the engine or burner. In order to avoid this problem, a sealant that is oil- or water-tight has been inserted between the pickup lead wire and the outer tube. However, the outer tube has air holes so that oil or water can enter the sensor through these holes.

SUMMARY OF THE INVENTION

The primary object, therefore, of the present invention is to provide an oxygen sensor which is capable of effective prevention of contamination of the inner conductive layer by oil or water.

The above-stated object of the present invention can be attained by an oxygen sensor which comprises an oxygen detecting element in a tubular form of a solid electrolyte which is closed at one end and open at the other end and which has a conductive layer deposited on both outer and inner surfaces. An output terminal has one end which is retained at the upper portion of the open end of said oxygen detecting element. An outer tube with air holes protects the oxygen detecting element and the output terminal. An air-permeable spacer is disposed between the output terminal and the area of the outer tube where the air holes are formed and which is molded from a mixture of an inorganic fiber and a thermoplastic resin.

BRIEF DESCRIPTION OF THE DRAWINGS

FIG. 5(a) is a front view of the oxygen sensor according to a fifth embodiment of the present invention, with half of the sensor being taken away; and FIG. 5(b) is a cross section taken on line E—E of FIG. 5(a)

DETAILED DESCRIPTION OF THE PREFERRED EMBODIMENTS

The oxygen sensor of the present invention will now be described with reference to the embodiment shown in the accompanying drawings.

Figure 1A:
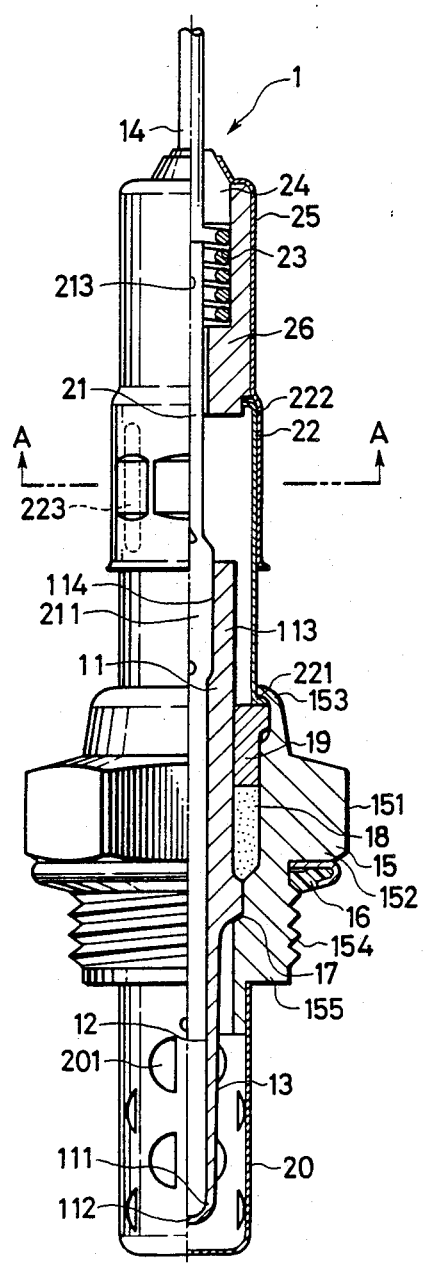
FIG. 1(a) is a front view of the oxygen sensor according to a first embodiment of the present invention, with half of the sensor being taken away.

FIG. 1(a) shows a first embodiment of the oxygen sensor of the present invention. An oxygen sensor 1 of the present invention is attached to a combustion source such as an internal combustion engine (not shown). An oxygen detecting element 11 in a tubular form of a solid electrolyte such as zirconia ($ZrO_2$) has a closed portion 112 at a lower end 111 and an open portion 114 at the other upper end 113. A platinum inner conductive layer 12 is deposited on the inner surface of the oxygen detecting element 11 by an appropriate technique such as evaporation. An outer conductive layer 13 is also made of platinum (Pt) and is deposited on the outer surface of the oxygen detecting element 11. A lead wire 14 is electrically connected to the inner conductive layer 12 for picking up an electrical output from this layer 12. A metal fixture 15 is electrically connected to the outer conductive layer 13 and is in a tubular form such that it is capable of accommodating the oxygen detecting element 11. The periphery 151 of the fixture 15 is provided with the head of a hexagonal bolt 152 and a male thread 154 which assist in attachment of the sensor 1 to the engine. A gasket 16 prevents leakage of the exhaust gas from between the sensor 1 and the wall (not shown) of the engine and is provided at the portion of the fixture 15 which is to make contact with the wall of the engine. The fixture 15 is also provided with a tightening area 153. By tightening this area 153, the oxygen detecting element 11 is securely held on the fixture 15 in cooperation with a packing sheet 17, talc 18 and a tightening ring 19 which are disposed on the inner peripheral surface of the fixture 15. A flange 221 on an inner tube 22 is also used in securing the oxygen detecting element 11. FIG. 1(a) also shows a protector 20 which is provided with a plurality of holes 201 for establishing communication between the exhaust gas and the outer conductive layer 13. The protector 20 protects the oxygen detecting element 11 by being fitted to the end 155 of the fixture 15 which is closer to the combustion chamber.

In FIG. 1(a), a metallic output terminal 21 is made of spring steel. The terminal penetrates through a hole 213 and provides electrical connection between the inner conductive layer 12 on the oxygen detecting element 11 and the pickup lead wire 14. In the embodiment under discussion, the output terminal 21 is formed of a bar of precipitation-hardened stainless steel (SUS 631). This terminal 21 has a junction 211 exhibiting resiliency in the radial direction and is electrically connected to the inner conductive layer 12 deposited on the inner surface of the upper opening 114 in the oxygen detecting element 11. In order to establish electrical connection to the inner layer 12, the junction 211 is pressed into the opening 114 and the pressure is then released, whereupon the terminal 21 is tightly held against the inner conductive layer 12. The junction 211 is protected by the inner tube 22. The output terminal 21 and the pickup lead wire 14 are connected to each other by compression.

Figure 1B:
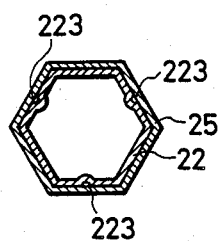
FIG. 1(b) is a cross section taken on line A—A of FIG. 1(a)

The junction between the terminal 21 and the lead wire 14 is protected by a protective outer tube 25 in such a manner that neither water nor oil will enter the oxygen sensor 1 of the present invention. The outer protective tube 25 loosely surrounds the inner tube 22 so as to permit the flow of atmospheric air, except where they form a close contact region of flat peripheral surfaces, shown in cross-section in FIG. 1(b). The outer tube 25 has a spring 23 and a sealant 24 which is fixed at the top end of the tube by the spring and through which the lead wire 14 penetrates. The sealant is made of thermoplastic polyethylene terephthalate [$(CF_2=CF_2)n$, known under the trademark Teflon]. A spacer 26 is pressed under the spring 23 and urges against the top end 222 of the inner tube 22. This spacer 26 is characterized as being molded from a fiberglass reinforced plastic, which is slightly resilient, has good creep resistance and exhibits high heat resistance. This plastic of the spacer 26 is a mixture of (1) highly air-permeable glass fibers having a porosity of 0.3–15% per unit cross-sectional area (the fibers typically having a diameter of 10 micrometers and a length of 100 micrometers and being mixed at a ratio of 30–50% by weight) and (2) polyethylene terephthalate (mixed at 50–70% by weight) which is a highly water repellent and heat resistant thermoplastic resin. The spacer 26 communicates with the atmospheric air through vertically extending passages 223 (shown also in FIG. 1(b)) formed between the inner and outer tubes 6 inward indentations in the inner tube 22 but prevents oil or water from permeating which would otherwise contaminate the inner conductive layer 12. Since there is no possibility of the corrosion of the inner conductive layer 12, the oxygen sensor 1 of the present invention ensures detection of the oxygen concentration in the exhaust gas for an extended period, with the inner conductive layer 12 and the outer conductive layer 13 being held in normal contact with the atmospheric air and the exhaust gas, respectively.

In the first embodiment described above, the output terminal 21 and the lead wire 14 are shown to be joined together by compression, but it should be understood that they may be joined by brazing or any other standard bonding techniques.

Figures 2A, 2B:
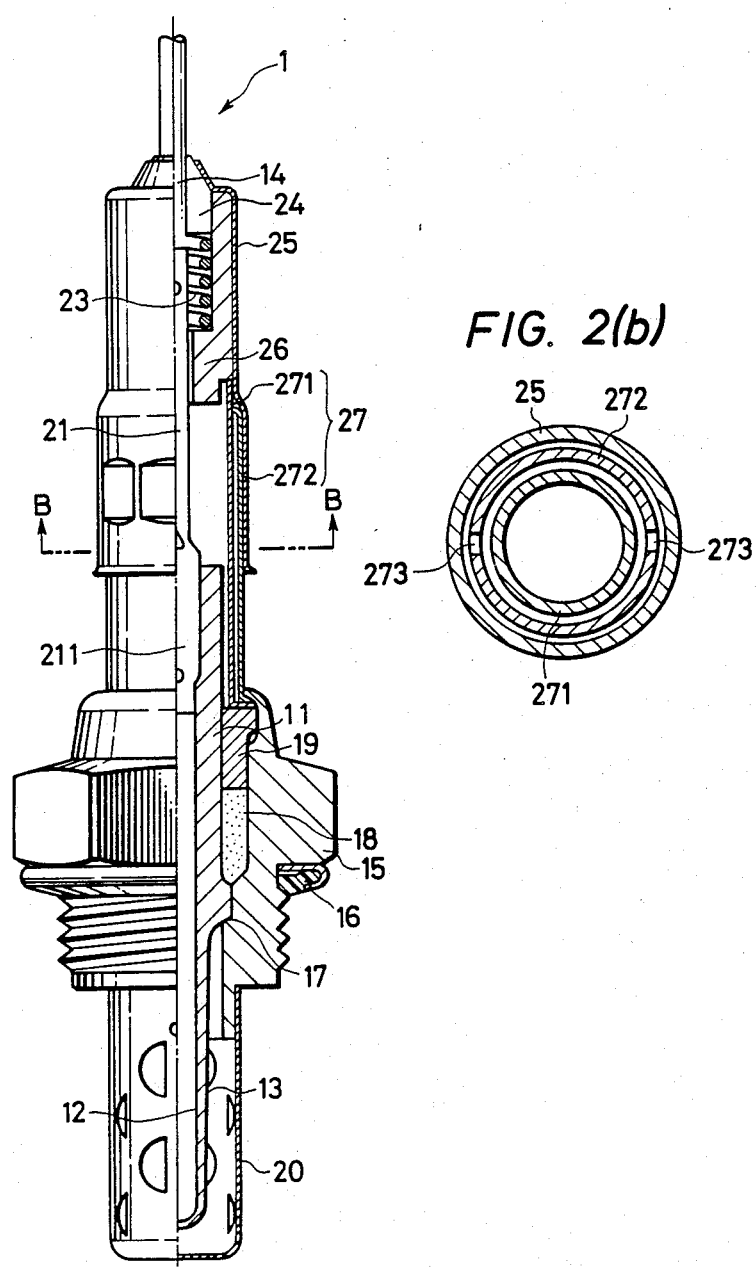
FIG. 2(a) is a front view of the oxygen sensor according to a second embodiment of the present invention, with half of the sensor being taken away.
FIG. 2(b) is a cross section taken on line B-B of FIG. 2(a)

FIGS. 2(a) and 2(b) shows a second embodiment of the oxygen sensor of the present invention. In the following description, the components which fulfill the same function as those shown in the first embodiment will be indicated by identical numerals.

The oxygen sensor 1 of the second embodiment also uses an inner tube 27 for protecting the junction 211 of the output terminal 21. This inner tube 27 consists of an inner pipe 271 and an outer pipe 272 spaced slightly apart from the outer tube 27, as shown in FIG. 2, away from the flat exterior surfaces. The outer pipe 272 has air holes 273 formed in its side below the flat surfaces for admitting the atmospheric air through the spacer 26 which is molded from a mixture of glass fiber and polyethylene terephthalate. When oil or water splashes over a heated oxygen sensor, the pressure in the sensor will drop sufficiently to suck the oil or water into the sensor. However, according to the second embodiment of the invention, the outer pipe 272 of the double-walled tube 27 serves as a buffer that allows the pressure in the oxygen sensor 1 to decrease only slowly. The second embodiment is particularly effective for minimizing the entrance of water which occurs when the oxygen sensor 1 is splashed with water at high operating temperatures.

Figure 3A:
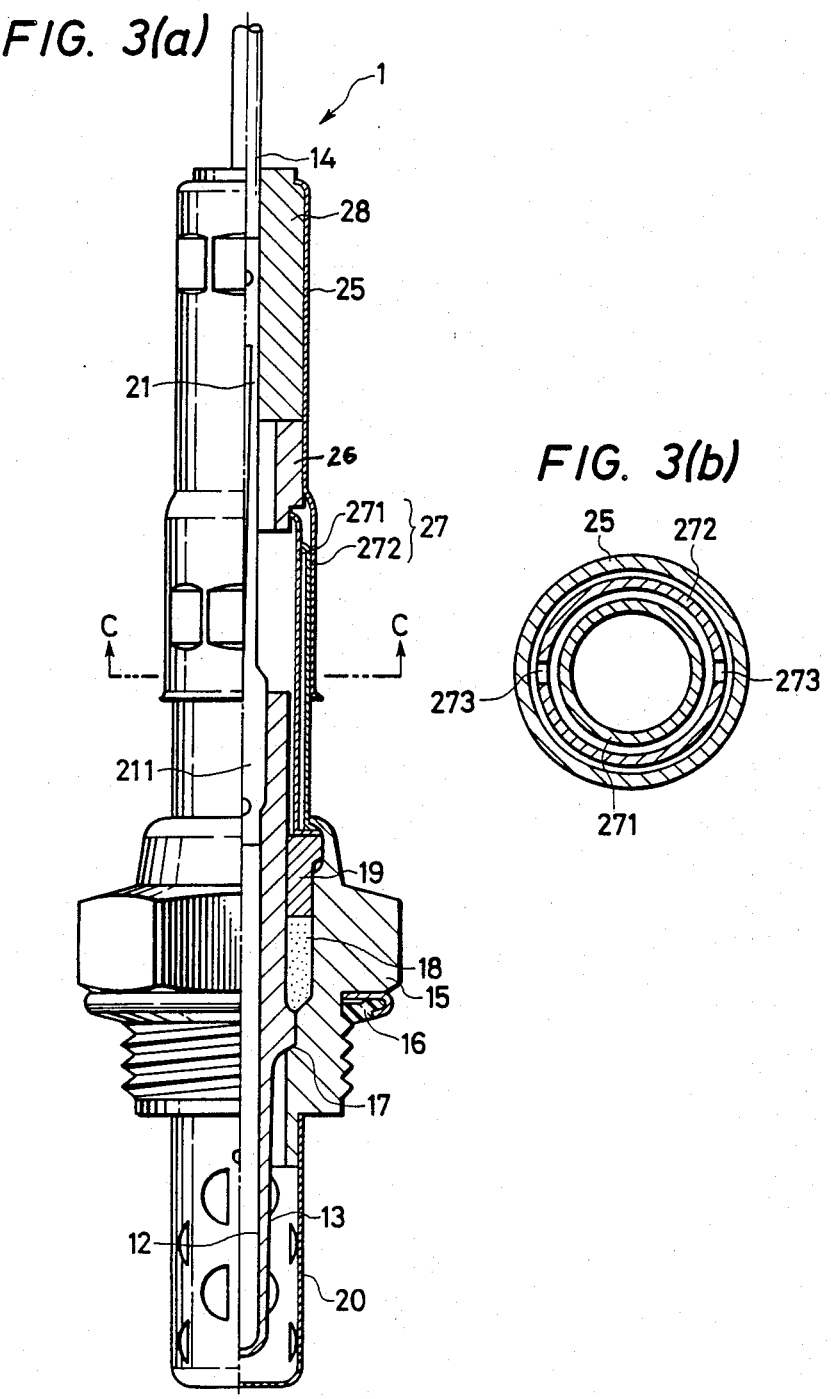
FIG. 3(a) is a front view of the oxygen sensor according to a third embodiment of the present invention, with half of the sensor being cut away.
Figure 3B:
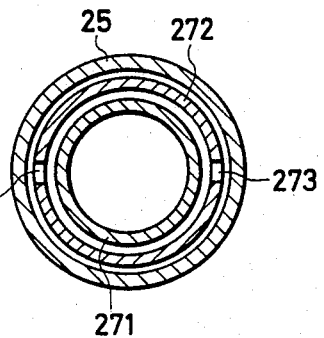
FIG. 3(b) is a cross section taken on line C—C of FIG. 3(a)

FIGS. 3(a) and 3(b) show a third embodiment of the oxygen sensor of the present invention. The oxygen sensor 1 of the second embodiment uses a tubular sealant 28 made of silicone rubber (SI) which is functional over a wide range of temperatures and exhibits high flexibility even at $-90°$ C. while maintaining high heat resistance. This sensor is more effectively sealed than the sensor 1 in the first embodiment and is highly immune to faulty operation which will otherwise be caused by the entrance of water or oil into the sensor.

Figure 4A:
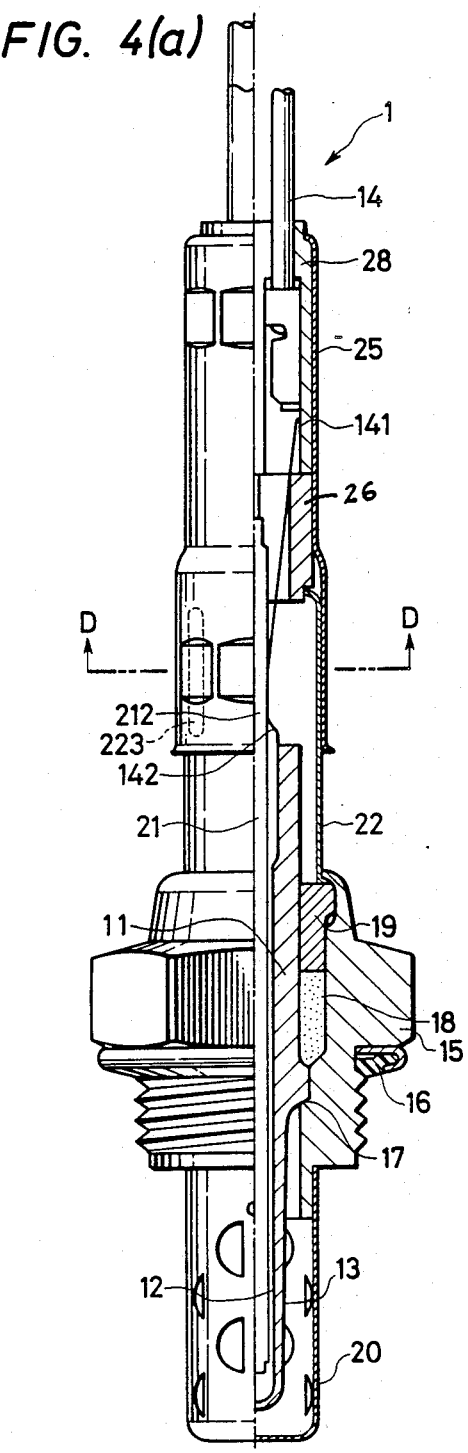
FIG. 4(a) is a front view of the oxygen sensor according to a fourth embodiment of the present invention, with half of the sensor being cut away.
Figure 4B:
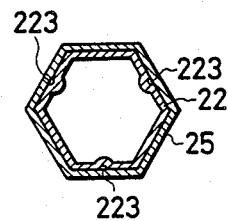
FIG. 4(b) is a cross section taken on line D—D of FIG. 4(a)

FIGS. 4(a) and 4(b) show a fourth embodiment of the oxygen sensor of the present invention. In the oxygen sensor 1 of this embodiment, the pickup lead wire 14 has a core 141 which is connected to the end portion 212 of the output terminal 21 which in turn is connected to the inner conductive layer 12 by a core 142.

FIG. 5(a) and 5(b) show a fifth embodiment of the oxygen sensor of the present invention. In the oxygen sensor 1 of this embodiment, the inner tube 27 for protecting the outer portion 212 of the output terminal 21 consists of an inner pipe 271 and an outer pipe 272 and has air holes 273, formed in the side of the outer pipe 272 for admitting the atmospheric air through the spacer 26 which is molded from a mixture of glass fiber and polyethylene terephthalate. Because of the use of the dual-walled outer tube 27, the oxygen sensor 1 of the fifth embodiment attains the same advantage as the sensor of the second embodiment.

The oxygen sensor of the present invention having the construction described above displays the following advantages.

A spacer having high air-permeability and water repellency and which is molded from a mixture of an inorganic fiber and a thermoplastic resin is provided between the output terminal and the area of the outer tube where air holes are formed. Therefore, when the oxygen sensor is attached to an internal combustion engine or a burner in such a manner that the inner conductive layer is in contact with the atmospheric air and the outer conductive layer in contact with the exhaust gas from the engine or burner, the sensor permits the concentration of oxygen in the exhaust gas to be detected while avoiding contact between oil or water and the inner conductive layer by virtue of the spacer. Since the inner conductive layer is not attacked by oil or water, the sensor is immune to faulty operation due to corrosion and ensures correct detection of the oxygen concentration in the exhaust gas over an extended period.

What is claimed is:

1. An oxygen sensor comprising:
   an oxygen detecting element in a tubular form of a solid electrolyte which is closed at a lower end and opened at the other upper end and which has a conductive layer deposited on both outer and inner surfaces;
   an output terminal, one end of which is retained at an upper portion of the open end of said oxygen detecting element;
   a first tube which surrounds and protects said oxygen detecting element and said output terminal;
   a second tube having a lower end portion surrounding an upper end portion of said first tube, vertical air flow passages being provided between said first and second tubes and extending to the uppermost end of said first tube so that the length of said air flow passage is maximized; and
   air-permeable, water- and oil-impermeable spacer means having a lower end abutting against an uppermost end of said first tube and having an upper end fitted into an upper end of said second tube, said spacer means circumscribing said output terminal for insulating said output terminal and covering uppermost ends of said vertical air flow passages, for permitting atmospheric air to flow therethrough while blocking oil and water, said spacer means being molded from a mixture of an inorganic fiber and a thermal plastic resin.

2. An oxygen sensor according to claim 1, wherein said spacer means is made of a fiberglass reinforced plastic which is mixture of glass fiber and polyethylene terephthalate.

3. An oxygen sensor according to claim 1, wherein said spacer means has a porosity within the range of 0.3 –15% per cent cross sectional area.

4. An oxygen sensor according to claim 1, wherein said air flow passages are formed by a plurality of vertically extending indentations in said upper end portion of said first tube.

5. An oxygen sensor according to claim 1, wherein said first tube has spaced apart inner and outer walls, and wherein said air flow passages further include at least one hole in said outer wall disposed below said circumferential area and below said spacer means.

6. An oxygen sensor according to claim 1, wherein said spacer means has a circumferential step formed in an outer surface thereof, said upper end of said second tube resting on said step; and further comprising spring means urging said spacer means in a lower direction against said upper end of said second tube.

* * * * *